(12) United States Patent
Sjostrom et al.

(10) Patent No.: US 6,260,210 B1
(45) Date of Patent: Jul. 17, 2001

(54) MEASURING MEANS FOR CHECKING THE CIRCUMFERENTIAL SIZE OF A BODY PORTION

(75) Inventors: Lars Sjostrom; Leni Sjostrom, both of Hovas (SE)

(73) Assignee: Lenimen AB, Hovas (SE)

( * ) Notice: Subject to any disclaimer, the term of this patent is extended or adjusted under 35 U.S.C. 154(b) by 0 days.

(21) Appl. No.: 09/402,823

(22) PCT Filed: Apr. 9, 1998

(86) PCT No.: PCT/SE98/00660

§ 371 Date: Nov. 29, 1999

§ 102(e) Date: Nov. 29, 1999

(87) PCT Pub. No.: WO98/46134

PCT Pub. Date: Oct. 22, 1998

(30) Foreign Application Priority Data

Apr. 12, 1997 (SE) .................................................. 9701380

(51) Int. Cl.⁷ ...................................................... A41F 9/00
(52) U.S. Cl. ...................................................... 2/321; 2/325
(58) Field of Search ............................. 2/321, 322, 311, 2/324, 325, 326, 338, 339, 2.11; 24/615, 616, 16 PB, 17 AP, 17 R, 585

(56) References Cited

U.S. PATENT DOCUMENTS

| 3,102,311 | * | 9/1963 | Martin et al. | 24/16 |
| 5,572,747 | * | 11/1996 | Cheng | 2/322 |
| 5,579,563 | * | 12/1996 | Sim | 23/585 |
| 5,588,186 | * | 12/1996 | Ko | 24/585 |
| 5,687,456 | * | 11/1997 | Chang | 24/16 PB |
| 5,749,127 | * | 5/1998 | Hsieh | 24/3.13 |
| 5,826,308 | * | 10/1998 | Chang | 24/16 PB |
| 5,956,813 | * | 9/1999 | Cooper | 24/16 PB |
| 6,067,662 | * | 5/2000 | Sim | 2/339 |
| 6,070,304 | * | 6/2000 | Lii | 24/16 PB |
| 6,105,908 | * | 8/2000 | Kraus | 24/16 PB |

FOREIGN PATENT DOCUMENTS

| 2 278 278 | 2/1976 | (FR) . |
| 503 628 | 7/1996 | (SE) . |

* cited by examiner

*Primary Examiner*—John J. Calvert
*Assistant Examiner*—Tejash Patel
(74) *Attorney, Agent, or Firm*—Young & Thompson

(57) ABSTRACT

The present invention relates to a waist band of a non-stretchable material intended as an aid to weight reduction and long-term maintenance of a weight reduction and as an aid to preventing fatness in persons of normal weight. The waist band (1) is characterized in that it is provided with a clasp (2) in the form of a one-way lock which only allows tightening of the band (1) around the waist but which does not allow for loosening thereof.

11 Claims, 4 Drawing Sheets

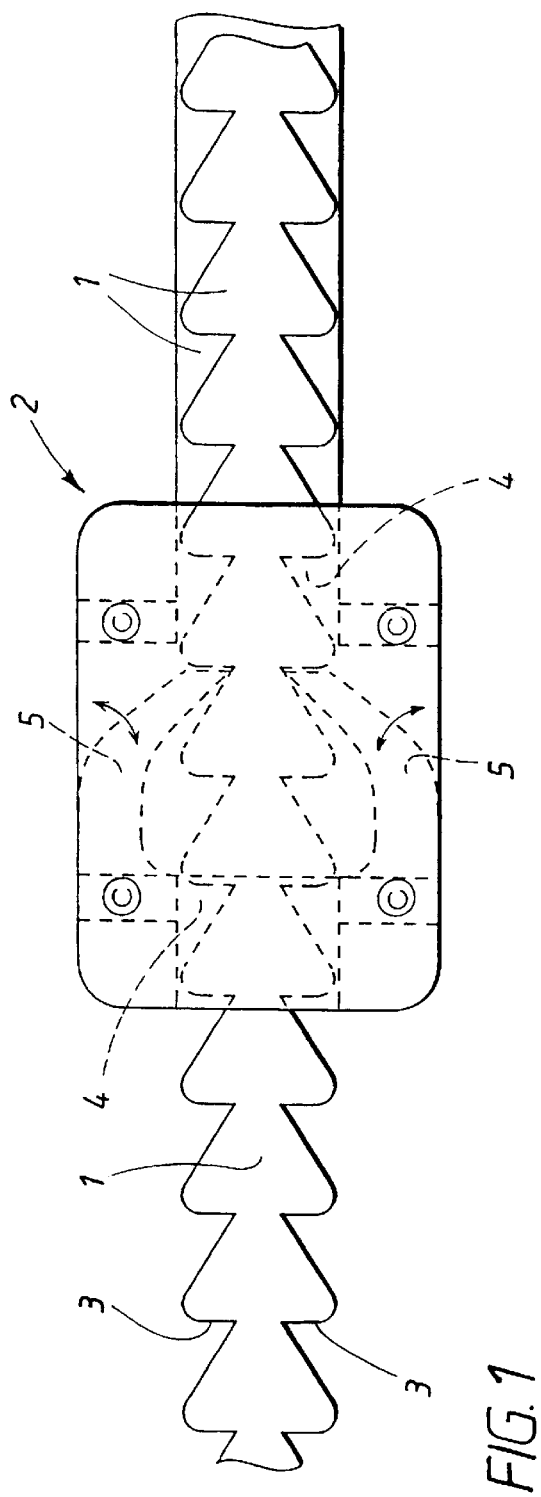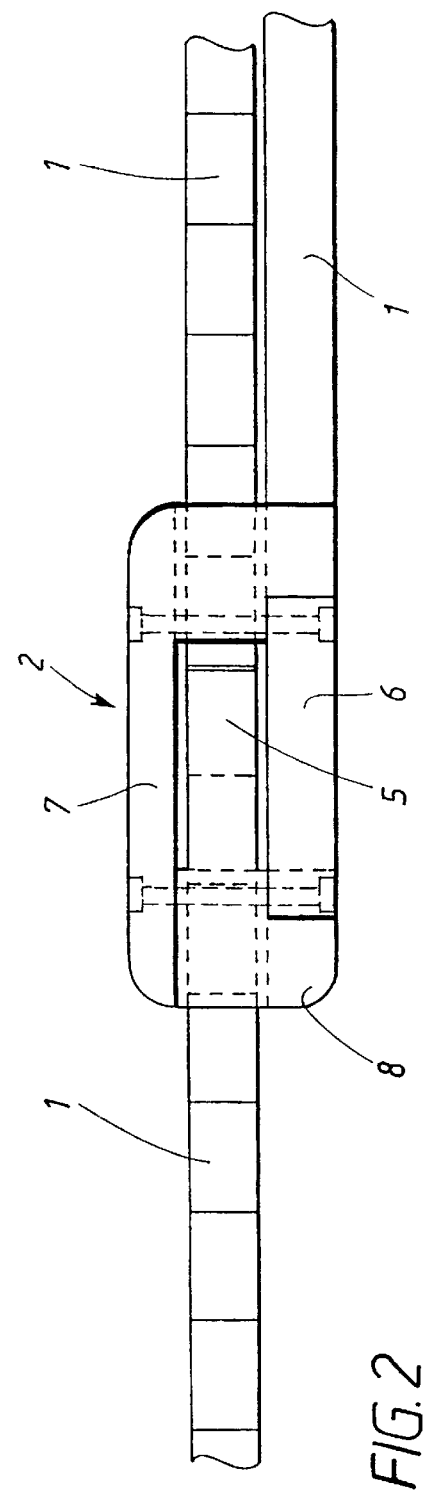

Figure 5:
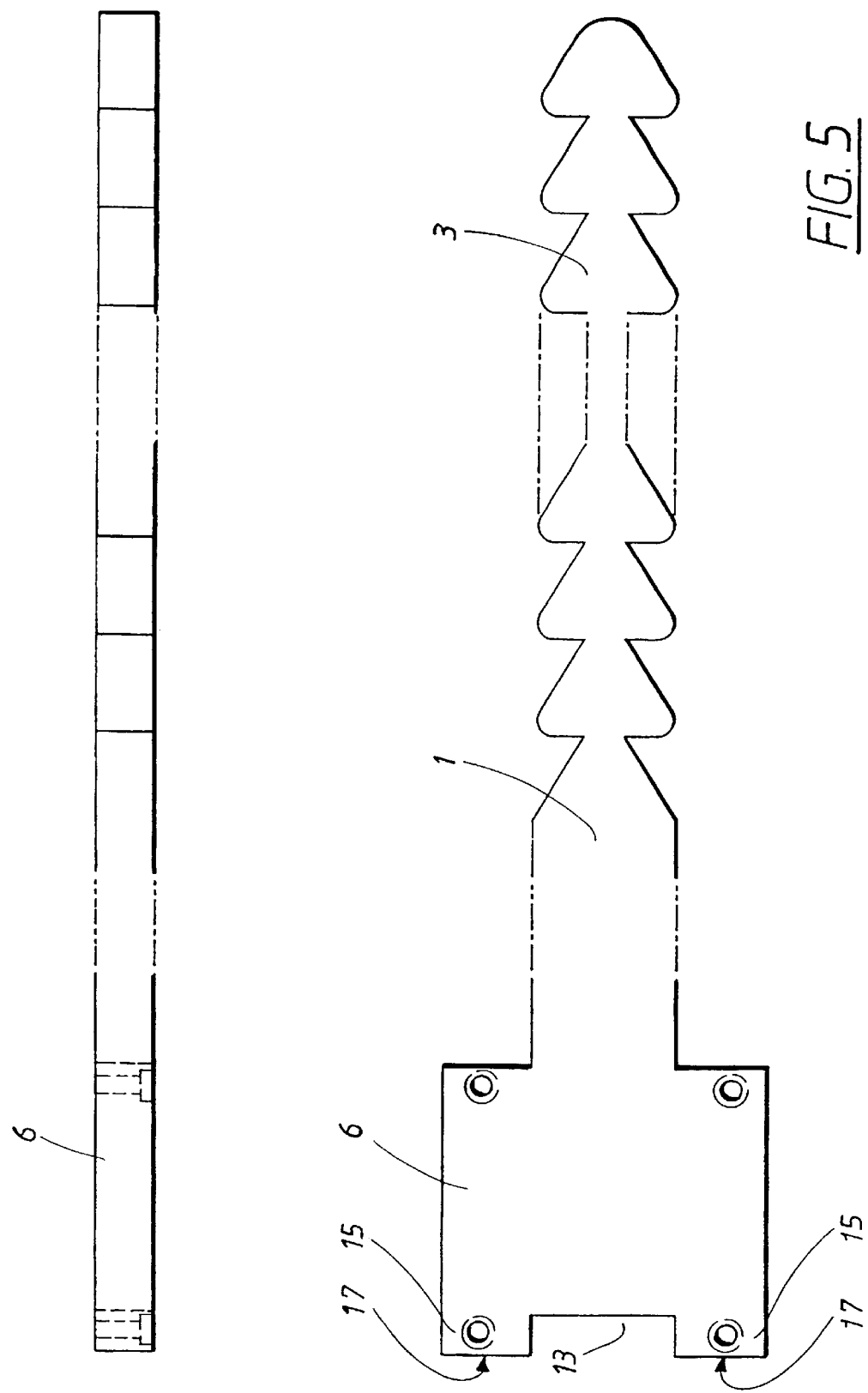

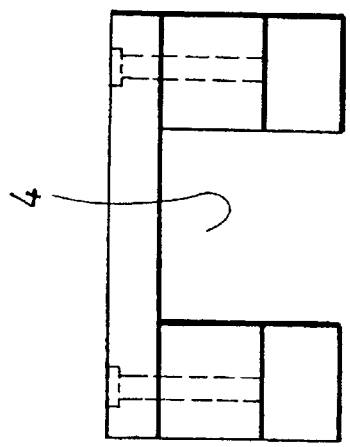
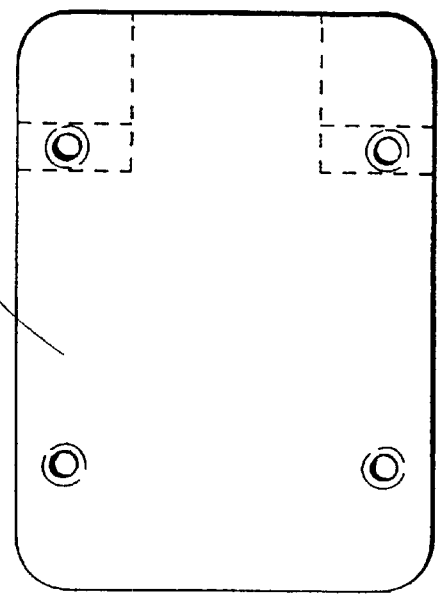
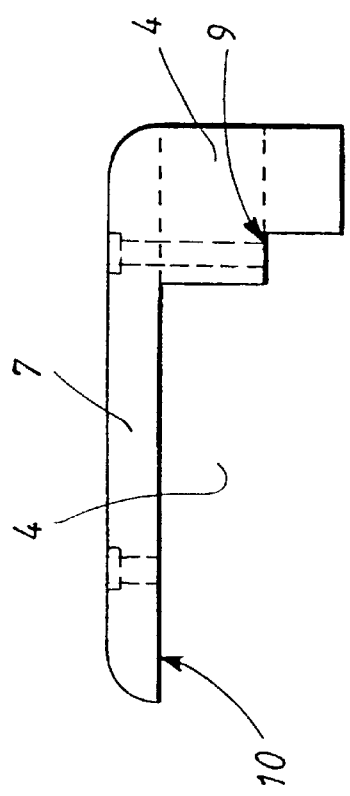
FIG. 3

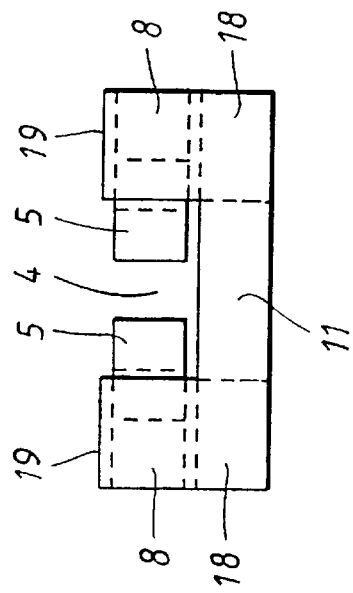
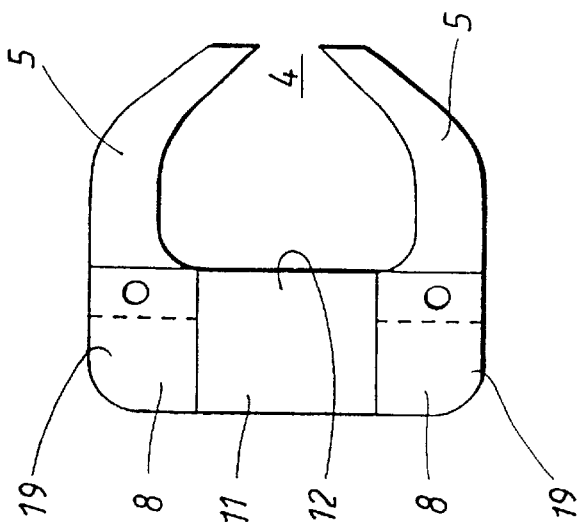
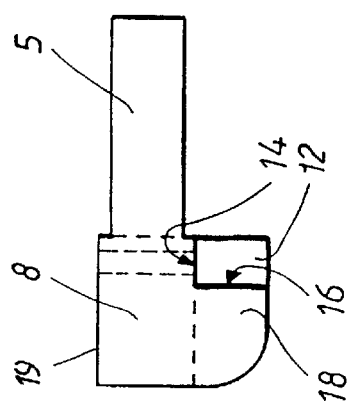
FIG.4

MEASURING MEANS FOR CHECKING THE CIRCUMFERENTIAL SIZE OF A BODY PORTION

TECHNICAL FIELD

The present application relates to a waist band having a one-way lock and a centimeter indication intended as an aid to weight reduction and long-term weight control.

The waist band is provided with a one-way lock which is designed in such a way that the effective waist circumference can be maintained constant or reduced but never increased. The band is intended to be used as an aid during weight reduction, as an aid for long-term weight control after weight reduction and as an aid to preventing fatness. The waist band, which may be produced in different versions for men and women, can be provided with markings for normal, moderate and great increases in waist circumference, and also with centimeter indications which allow the waist circumference to be read.

BACKGROUND OF THE INVENTION

Fatness is a serious and common health problem in the whole western world. Certain surgical operations of the stomach or the intestine result in large and permanent weight reductions but these measures are associated with high costs, substantial discomfort and certain risks. Some conventional weight reduction methods can give short-term weight reductions but no currently known non-surgical methods can give permanent weight reduction for a majority of treated greatly overweight individuals. A basic reason for the poor long-term results is that the overweight persons are unable to make a life-long change of lifestyle. Such a change of lifestyle should in principle have to be applied every day during the rest of one's life after a weight reduction. The registering of the body weight every morning and the introduction of a so-called monitor weight which should not be exceeded is a usual way to make individuals who have lost weight aware of the need for a permanent change of lifestyle. Persons who have lost weight are encouraged to introduce a strict restriction of calories every day the body weight exceeds the monitor weight. Already the next day the person will then usually be on the right side of his or her monitor weight. Many correctly instructed patients manage the above-described or similar regimes for some months, but less than 10% of the treated persons succeed in maintaining their weight reduction for 24 months. Persons with a tendency towards fatness are evidently in need of support from more tangible aids than a scale to be able to manage their weight control in the long term.

Degrees of over- or underweight are traditionally indicated in so-called BMI-units (Body Mass Index). BMI is calculated as (body weight in kilograms)/(bodylength in m)$^2$. The normal area for BMI is 20–25 kg/M$^2$. Overweight exists between 25 and 30 kg/m$^2$ and individuals having a BMI>30 kg/M$^2$ are classified as obese or fat. A BMI of 25 kg/m$^2$ corresponds to a waist circumference of about 89 cm in adult men and about 80 cm in adult women. The body length has surprisingly no significant influence on the waist circumference. A great number of epidemiological studies have shown that poor health, mortality and so-called risk factors for cardio-vascular disease (increased blood sugar, insulin, blood fats, blood pressure etc.) increase both with increasing BMI and with increasing waist circumference. Consequently, the waist circumference, like BMI, is both an indicator of overweight and a risk indicator.

In a majority of western populations the average body weight increases between the age of 20 and 60 years. This weight increase, which is associated with bad health should, if possible be prevented.

Own (Lars Sjöström) unpublished sensitivity- and specificity data from combined normal weight and overweight populations indicates that a waist circumference of 94 (men) and 82 (women) cm, respectively, would be desirable upper normal values from a risk point of view. These waist circumferences are associated with moderate overweight. At waist circumferences of 102 (men) and 90 (women) cm, respectively, obvious overweight exists and also increased cardio-vascular risk in the majority of individuals.

The Solution:

According to the present invention, an auxiliary means for solving the above problems has been brought about and a waist band of non-stretchable material intended as an aid to weight reduction and long-term maintainance of weight reduction has been constructed and the invention is characterized in that the band is provided with a clasp in the form of a one-way lock which only allows tightening of the band around the waist but which does not allow for loosening thereof.

According to the invention, the lock includes a passage for the free end of the band which on one or both sides or all around is provided with barbs, teeth or the like and the passage on one or both sides or all around is provided with one or more resilient counterhooks intended to cooperate with the barbs, the teeth or the like and lock the waist band against being drawn backwards out of the lock.

According to the invention, the lock with its passage may be mounted on, under or at the side of the waist band in its locking end.

According to the invention, the band may have a square, rectangular, triangular, round, oval or polygonal sectional area.

The band can also, according to the invention, consist of a chain or a tube.

According to the invention, it is suitable that the lock consist of a bottom plate from which the band starts, a cover having a passage for the free end of the band and a part lying therebetween having a passage and resilient hooks at either side of the passage.

As stated above, the waist band is provided with a one-way lock, which has been designed so that the effective waist circumference of the band can only be maintained unchanged or reduced but cannot be increased. The band is applied around the waist at the beginning of a weight reduction and is tightened as the waist circumference is reduced. The excess band which has passed the locking mechanism is cut off regularly. The band shall not be drawn too tightly but only so much that it comfortably conforms to the waist. In the event of a weight increase, the band will immediately be felt and the patient will have to choose between reducing calory intake (alternatively, increasing physical activity) or cutting off the band. Common psychological mechanisms indicate that many patients would be reluctant to cut off the waist band and, by doing so, in a marked way give up the weight struggle. Thus the waist band would work as a long-term automatically supporting aid for many individuals who cannot manage to maintain the attained weight reductions in a more traditional way. In the same way, the band could be used to prevent the weight increase which commonly occurs in middle age.

The band is produced from skin-friendly material and so formed that it does not give rise to any skin irritations. If the wearer of the band, in spite of reminders from the band, increases in weight, the band shall be cut off and removed before it causes skin damage.

Obese persons do not have any waist. The band is then placed above the stomach at the lower part of the chest. When a weight reduction has resulted in a waist, the band should be placed there, i.e. between the hip bone and the lower part of the chest, as these anatomic structures can be felt at the side of the trunk.

FIGURE DESCRIPTION

The invention will in the following be described more in detail in connection with the drawings enclosed in which:

FIG. 1 shows a band in a mounted state seen from above when it is imagined to lie on a table or the like, in which FIG. 2 shows the same as in FIG. 1 but seen from the side, in which FIG. 3 shows a cover of the lock seen from two sides and from above, in which FIG. 4 shows an intermediate part with the resilient counterhooks in the lock seen from two sides and from above and in which FIG. 5 shows the bottom part of a lock according to the invention seen from the side and from above.

DETAILED DESCRIPTION:

In FIG. 1 a band 1 is shown which is attached in a locking mechanism 2 in a suitable way and which is intended to make a loop around a waist and therefore comes back on the other side of the locking mechanism 2 to be pushed therein and come out with a suitable length, for example above the outgoing band. As appears from the figure, the outgoing part of the band is smooth, whereas the ingoing part of the band 1 into the locking mechanism 2 is provided with barbs or teeth 3.

In the locking mechanism 2 a through-going passage 4 is present so that the band 1 can be moved in through the locking mechanism 2. To prevent the band 1 from being drawn back out of the locking mechanism 2, two outwardly resilient counterhooks 5 are, according to the present embodiment, arranged on an intermediate piece in the lock 2. When the barbed band is drawn through the locking arrangement 2 to the right in the figure, these counterhooks will be swung outwardly due to contact with the band 1 and will fall into the recesses between the barbs after a certain length has been drawn. Since these locking hooks cannot be moved outwardly without drawing the band 1 to the right, it is not possible to draw the band to the left. Accordingly, it is barred against moving in that direction.

FIG. 2 shows the same arrangement as the one according to FIG. 1 seen from the side. The locking arrangement 2 has here a bottom plate 6 which in the present case is screwed to a cover 7 by means of four countersunk screws, or the like. The parts may of course also be glued together or attached to each other in some other way. Between the cover 7 and the bottom part 6 two holders 8 for the outwardly swingable counterhooks 5 are arranged.

FIG. 3 shows more in detail the cover 7. The passage 4 exists therein. The cover is at the surface 9 intended to abut against the bottom part and at the surface 10 against the holders 8 for the counterhooks 5.

FIG. 4 shows the holders 8 with the counterhooks 5. The holders 8 are kept together by an intermediate piece 11 which in its right part consists of the heel 12. The heel 12 fits in the recess 13 of the bottom plate (FIG. 5). The holders 8 have a recess with a surface 14 which shall abut against the surface 15 of the bottom plate and a surface 16 which shall abut against the surface 17 of the bottom plate. Accordingly, the recess creates in the lower, outer part of the holders 8 a heel 18. The heels 12 and 18 guarantee that the holders 8 are mounted correctly in relation to the bottom plate 6 and prevent the holders and counterhooks from being drawn to the right in the lock when the band passes through the lock. The surface 19 is the one that shall abut against the surface 10 of the cover 7.

Finally, FIG. 5 shows the bottom plate 6 from which the band 1 starts. The band may be attached in any way in the bottom plate 6, for example by screwing, but it may also be made integrally with the bottom piece. The band 1 is suitably smooth along the major part of its length but has barbs 3 on a suitably long length of the free end. The smooth part can suitably be 70–80 cm and the part provided with barbs from 40–200 cm. The bottom plate 6 is suitably square and on that side where the band 1 shall re-enter the lock it has a recess 13 for the heel 12 on the holders 8.

The waist band must be made of a non-stretchable material which does not irritate the skin. Both the waist band and the lock can be produced from gold, silver, stainless steel, other metals, plastics, glass fibre, polymers or from natural materials or combinations of one or more of said materials. For exclusive variants of the waist band the lock can be decorated with precious stones or other decorations.

The waist band may be provided with centimeter indications whereby the waist circumference is read at the entrance to the lock.

In a plastics version for men, the waist band may for example be produced with a green field between 80–94 cm waist size, yellow between 94–102 cm and in red above 102 cm. Corresponding colour-circumference ratios for women may be 70–82 cm, 82–90 cm or more than 90 cm. These colour-circumference ratios may be revised if more accurate epidemiological data are produced.

If precious metals or other embodiments are used the above colour-distance ratios may be marked in some other suitable way.

The invention is not limited to the shown embodiment but can be varied in different ways within the scope of the claims.

What is claimed is:

1. Waist band of non-stretchable materials intended as an aid to weight reduction, to long-term maintainance of a weight reduction and to preventing fatness in persons having normal weight, characterized in that the band (1) has a first end which is attached to a first side of a one-way locking mechanism (2) and has a second, free end which is adapted for encircling the waist of a wearer and which is locked in the one-way locking mechanism (2) by insertion of the second end of the band (1) into a second side of the locking mechanism (2) which is opposite to the first side of the locking mechanism (2) so that the first and second ends of the waist band (1) are parallel to each other when the second end is inserted in the locking mechanism (2) and that the one-way locking mechanism (2) only allows tightening of the band (1) around the waist but does not allow loosening thereof.

2. Waist band according to claim 1, characterized in that the lock (2) includes a passage (4) for the free second end of the band (1) which on one or both sides or all around is provided with barbs (3) or teeth and that the passage (4) on one or both sides or all around is provided with one or more resilient counterhooks (5), intended to cooperate with the barbs or the teeth (3) and lock the band (1) against being drawn backwards out of the locking mechanism (2).

3. Waist band according to claim 2, characterized in that the locking mechanism (2) with its passage (4) is mounted at the side of the waist band (1).

4. Waist band according to claim 2, characterized in that the locking mechanism (2) with its passage (4) is mounted on or under the waist band (1).

5. Waist band according to claim 2, characterized in that the locking mechanism (2) consists of a bottom plate (6), from which the band starts, a cover (7) with the passage (4) for the free second end of the band (1) and including holders (8) bearing resilient counterhooks (5) and being arranged on either side of the passage (4) between the bottom plate (6) and the cover (7).

6. Waist band according to claim 1, characterized in that the waist band (1) has a square, rectangular, triangular, round, oval or polygonal section surface.

7. Waist band according to claim 1, characterized in that the band (1) consists of a chain or a tube.

8. A method of assisting in weight reduction, the method comprising the steps of:

extending a non-stretchable waist band around a waist of a person in need of assistance in weight reduction, the waist band having a first end which is attached to a first side of a one-way locking mechanism; and inserting a second free end of the waist band into a second side of the one-way locking mechanism that is opposite the first side of the one-way locking mechanism so that the first and second ends of the waist band are parallel to each other, the one-way locking mechanism allowing tightening of the waist band around the waist and not allowing loosening of the waist band.

9. The method of claim 8, wherein the inserting step comprises the steps of inserting the second free end into a passageway in the second side of the one-way locking mechanism and preventing withdrawal of the second free end from the passageway, the second free end having barbs on a side thereof and the passageway having a counterhook that engages the barbs to prevent withdrawal of the second free end from the passageway.

10. The method of claim 9, wherein the one-way locking mechanism has a flat bottom plate from which the first end extends and that forms a bottom of the passageway and a flat top plate that forms a top of the passageway, wherein the counterhook is between the top and bottom plates, and wherein the step of inserting the second free end into the passageway comprises the step of inserting the second free end between the top and bottom plates.

11. The method of claim 8, wherein the waist band has a flat surface and the one-way locking mechanism has a flat bottom and wherein the extending step includes the step of laying the flat bottom of the one-way locking mechanism and the flat surface of the waist band flat on the waist so that the waist band lies flat completely around the waist.

* * * * *